United States Patent [19]

Aspden et al.

[11] Patent Number: 5,147,802
[45] Date of Patent: Sep. 15, 1992

[54] PROCESS FOR EVALUATING CRACK PROPAGATION DUE TO CORROSION

[75] Inventors: Robert G. Aspden, Franklin Township, Westmoreland County; Thomas G. Bengel, Plum Borough, both of Pa.

[73] Assignee: Westinghouse Electric Corp., Pittsburgh, Pa.

[21] Appl. No.: 629,260

[22] Filed: Dec. 18, 1990

[51] Int. Cl.[5] .................... G01N 17/00; G01N 17/04
[52] U.S. Cl. ........................................ 436/6; 422/53; 73/53.01; 73/104
[58] Field of Search ............... 422/53; 436/6; 73/61.2, 73/104, 799, 819, 856, 859, 53

[56] References Cited

U.S. PATENT DOCUMENTS

| | | | |
|---|---|---|---|
| 3,349,495 | 6/1965 | Zemberry | 73/104 |
| 4,090,489 | 4/1985 | Barker | 73/799 X |
| 4,610,157 | 9/1986 | Vicki et al. | 73/104 X |
| 4,677,855 | 7/1987 | Coffin, Jr. et al. | 73/799 |
| 4,711,131 | 12/1987 | Hopkins | 73/799 |

*Primary Examiner*—James C. Housel
*Assistant Examiner*—Arlen Soderquist
*Attorney, Agent, or Firm*—M. G. Panian

[57] ABSTRACT

A test specimen for evaluating crack propagation and associated wear and corrosion on cladded piping is provided. The test specimen simulates the hairline crack conditions found on the inner cladding layer of a piping system. The test specimen is useful in analyzing the effects that a certain process fluid has on an exposed cracked cladding layer surface.

4 Claims, 1 Drawing Sheet

PROCESS FOR EVALUATING CRACK PROPAGATION DUE TO CORROSION

BACKGROUND OF THE INVENTION

1Field of the Invention

The present invention relates to the field of test specimens for evaluating crack propagation due to corrosion. More specifically, the invention relates to a unique apparatus and method for testing the effects of a corrodant upon a structure which has a support base and a cracked cladding layer deposited thereto.

2. Description of the Prior Art

The problem of excessive personnel exposures caused by high background radiation levels in a nuclear reactor primary system, such as in pressurized water reactor (PWR) systems, and the resultant economic cost of requiring personnel rotation to minimize individual exposure is significant at many nuclear plants. These background levels are principally due to the buildup of corrosion products in certain areas of the plant. The buildup of corrosion products exposes workers to high radiation levels during routine maintenance and refueling outages. The long term prognosis is that personnel exposure levels will continue to increase.

As a nuclear power plant operates, the surfaces in the core and primary system corrode. Corrosion products, referred to as crud, are activated by transport of the corroded material to the core region by the reactor coolant system (RCS). Subsequent release of the activated crud and redeposition elsewhere in the system produces radiation fields in piping and components throughout the primary system, thus increasing radiation levels throughout the plant. The activity of the corrosion product deposits is predominately due to Cobalt 58 and Cobalt 60. It is estimated that 80–90% of personnel radiation exposure can be attributed to these elements.

One way of controlling worker exposure, and of dealing with this problematic situation, is to periodically decontaminate the nuclear steam supply system using chemicals, thereby removing a significant fraction of the corrosion product oxide films. Prior techniques had done very little to decontaminate the primary system as a whole, typically focusing only on the heat exchanger (steam generator) channel heads.

Two different chemical processes, referred to as LOMI (developed in England under a joint program by EPRI and the Central Electricity Generating Board) and CAN-DEREM (developed by Atomic Energy of Canada, Ltd.), have been used for small scale decontamination in the past. These processes are multi-step operations, in which various chemicals are injected, recirculated, and then removed by ion-exchange. Although the chemicals are designed to dissolve the corrosion products, some particulates are also generated. While these chemical processes had typically been used on only a localized basis, use of these chemical processes has now been considered for possible application on a large scale, full system chemical decontamination as set forth in a co-pending application Ser. No. 07/621,120, filed Nov. 26, 1990, now U.S. Pat. No. 5,089,216, entitled "System For Chemical Decontamination Of Nuclear Reactor Primary Systems", and incorporated herein by reference.

One phase in the development of satisfactory dilute chemical decontamination (DCD) systems, such as CAN-DEREM and LOMI processes, is the study of the corrosive effects of DCD solutions on the materials and components in the RCS. There are components in the RCS that consist of carbon steel cladded with stainless steel on the exposed side. Thermal and mechanical stresses may cause small cracks to develop in the stainless steel cladding of these components.

Since it is known that these cracks exist, it is necessary to determine the corrosive effects of the DCD solutions which might penetrate through the cracks during the decontamination process. If the DCD solutions are corrosive in nature, they may impair the integrity of the underlying carbon steel.

Prior art testing specimens for studying the crack propagation in structures usually employed a bar type specimen. This specimen was rectangular in shape with a carbon steel base and a stainless steel surface. A crack was then cut into the stainless steel surface and the propagation of the crack was studied as stresses were applied to the surfaces. Such a specimen is ineffective to study the effects of corrodant penetration and subsequent possible crack propagation mainly because the crack extended to the edge of the test specimen and the sides of the test specimen were exposed to the corrodant. This condition would not occur in piping structures. Also, the crack cut into the stainless steel surface was much wider than an actual hairline crack which actually exists inside a piping structure located along the RCS. Therefore, a need exists to develop a testing specimen which could more accurately simulate the environment found in such cracked cladding systems.

SUMMARY OF THE INVENTION

The present invention is directed towards a test specimen which simulates the effects of a corrodant on a structure having a support base and a cracked cladding deposited onto the support base. The design defects of the prior art testing specimens are overcome in the inventive test specimen by creating a crack upon the surface of the cladding layer which does not extend to the edge of the cladding layer and which thereby prevents the corrodant test fluid from accessing the support base below the crack from somewhere other than the crack formed on the cladding surface.

The crack is formed on the cladding surface by first cutting a narrow slot into the cladding surface and optionally extending into the support base. This slot is closed off to create a hairline crack by forcing a wedge into an adjacent shallow slot. This shallow slot preferably extends only into the cladding surface.

The inventive test specimen comprises a support base and at least a first cladding layer deposited upon the support base which creates a first interface between the first cladding layer and the support base. A multitude of cladding layers can be deposited in a progressive fashion upon the prior cladding layer to model the structure being studied. A first slot is cut into the cladding layer and may extend into the support base. A second slot is cut adjacent to the first slot which preferably extends only into the cladding layer. A closing wall is thus created between the first slot and the second slot. A wedge is then inserted into the second slot which causes the closing wall to partially close the first slot and form a hairline crack on the surface of the cladding layer.

The test specimen is utilized by applying the corrodant onto the cladding surface. In this way, the corrodant comes into direct contact with the hairline crack. Later, the specimen is disassembled and dissected along the axis of the specimen perpendicular to the crack to determine the extent of corrosion in the cladding layer and the support base beneath the cracked surface of the cladding layer.

It is an object of the present invention to provide a test specimen for determining the corrosive effects of a corrodant upon a structure which has a support base with a cracked cladding deposited thereto.

It is also an object of the present invention to provide a process for determining the corrosive effects of a corrodant upon a structure which has a support base with a cracked cladding deposited thereto.

DETAILED DESCRIPTION OF THE INVENTION

The inventive test specimen allows for the testing of the corrosion effects that a corrodant will have on a component which is comprised of a base material and a cladding material in which the cladding material has a hairline crack which may extend into the base material. Although the test specimen is readily adaptable for testing various types of base and cladding materials, the preferred embodiment is for testing metals. The test specimen is ideally suited for testing the corrosive effects by a corrodant fluid on a piping structure which has a cracked metal cladding over a base metal. The test specimen is more easily understood by making reference to the accompanying figures in which like numbers refer to like elements.

Figure 1:
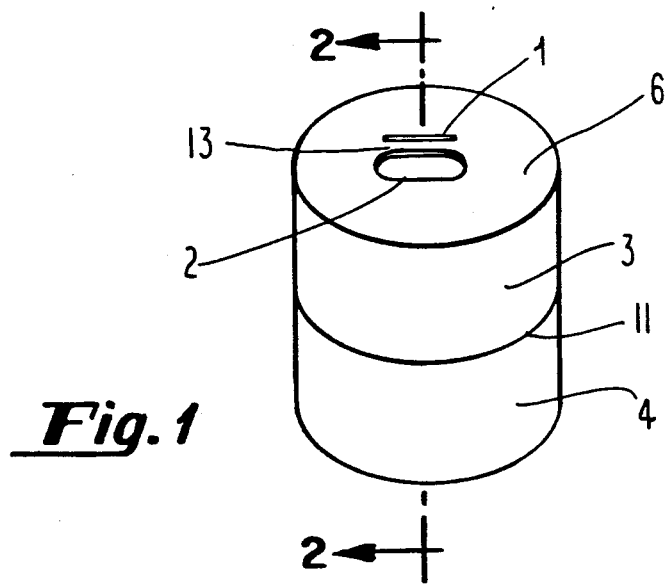
FIG. 1 is a perspective view of the inventive test specimen.

FIG. 1 displays a perspective view of the test specimen. A support base 4 has a cladding layer 3 deposited upon it. This creates an interface 11 between the support base 4 and the cladding layer 3. The preferred support base 4 is a metal, and most preferably carbon steel. The preferred cladding layer 3 is also a metal, and most preferably stainless steel. Although the inventive test specimen is directed towards a two layer material system, the embodiments of the test specimen could comprise a plurality of such material layers. The differing embodiments of the test specimen could comprise a multitude of compositions for each individual layer, such as metals, plastics, glass, etc., depending upon the system to be modeled by the test specimen.

Upon the cladding surface 6 is a crack slot 1 and an adjacent shallow slot 2. The crack slot 1 is cut so that it does not extend past the edge of the cladding layer 3. The shallow slot 2 is cut in close proximity to the crack slot 1 such that a closing wall 13 is established between the crack slot 1 and the shallow slot 2.

Figure 2:
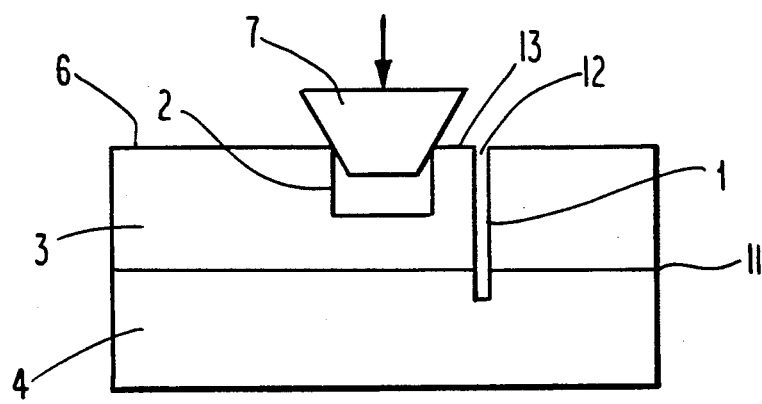
FIG. 2 is a cross sectional view of the inventive test specimen taken through line 2—2 of FIG. 1.

The test specimen can be described in greater detail by referring to a cross-sectional view as shown in FIG. 2. In order to simulate the minute hairline cracks which exist in the systems to be tested for corrosive resistance to corrodants, the crack slot 1 is cut into the cladding layer 3 and preferably extending into the support base 4. The depth of the crack slot 1 is dependent upon the system to be modeled. In the preferred embodiment, the crack is believed to extend into the interface 11 between the support base 4 and the cladding layer 3, therefore the crack slot 1 is made proportionally deep. The technique employed to generate the crack slot 1 will vary depending upon the composition of the support base 4 and the cladding layer 3. In the preferred embodiment where the support base is carbon steel and the cladding layer 3 is stainless steel, the technique employed is electrical discharge machining (EDM). This EDM technique has the ability to cut a crack slot 1 having a width from about 0.13 to 0.37 mm (0.005 to 0.02 in.). The shallow slot 2 does not require such a narrow width as the crack slot 1 and common milling techniques can be employed to create the shallow slot 2.

Adjacent to the crack slot 1, and in relatively close proximity, is the shallow slot 2. The shallow slot 2 is cut into the cladding layer 3 and preferable does not extend into the support base 4. Between the shallow slot 2 and the crack slot 1 is the closing wall 13.

In order to produce a simulated crack on the cladding surface 6 of a cladding material on a base material, the crack gap 12 formed by the creation of the crack slot 1 must be partially closed. A wedge 7 is therefore driven into the shallow slot 2 in order to force the closing wall 13 into the space created by the crack slot 1 thereby partially closing the crack gap 12. The wedge 7 is preferably a wedge shaped piece of metal, however a clamp inserted into shallow slot 2 with its prongs forcing outward against the walls of the shallow slot 2 could also be employed. This forms a crack 9, FIG. 3, which simulates the hairline crack found in the modeled system. The shallow slot 2 is preferably cut to extend past the front and rear end of the crack slot 1 so that the closing wall 13 extends the entire length of the crack slot 1.

The thickness of the support base 4 and the cladding layer 3 may be varied to represent the structure which is being studied for its corrosive effects. All of the other dimensions for the test specimen will also be dependent upon the structure being modeled.

For example, if a piping structure containing a stainless steel cladding over a carbon steel base is being studied, then the thickness of the test specimen can be correlated to that piping structure. If the piping structure has a carbon steel thickness of 9.5 mm (0.37 in.), then the support base 4 can also be made of that thickness of carbon steel. If the stainless steel cladding is 3.2 mm (0.13 in.) thick, then the distance from the cladding surface 6 to the interface 11 can also be 3.2 mm (0.13 in.) of stainless steel.

The shallow slot 2 can be cut to a depth of about 1.59 mm (0.06 in.). The shallow slot 2 can be approximately 12.7 mm (0.5 in.) long and 3.2 mm (0.12 in.) wide. The crack slot 1 is cut through the cladding layer 3 and preferably approximately 1.59 mm (0.06 in.) into the support base 4. The crack slot 1 can be about 6.3 mm (0.25 in.) long and about 0.25 mm (0.01 in.) wide when it is initially cut into the stainless steel surface. The closing wall 13 can have a width of about 0.38 mm (0.015 in.). The wedge 7 would have a width narrow enough to fit into the shallow slot 2 with an accompanying slope great enough to force the closing wall 13 into the crack gap 12 to result in a crack 9 having a width of 0.013 to 0.038 mm (0.0005 to 0.0015 in.).

Figure 3:
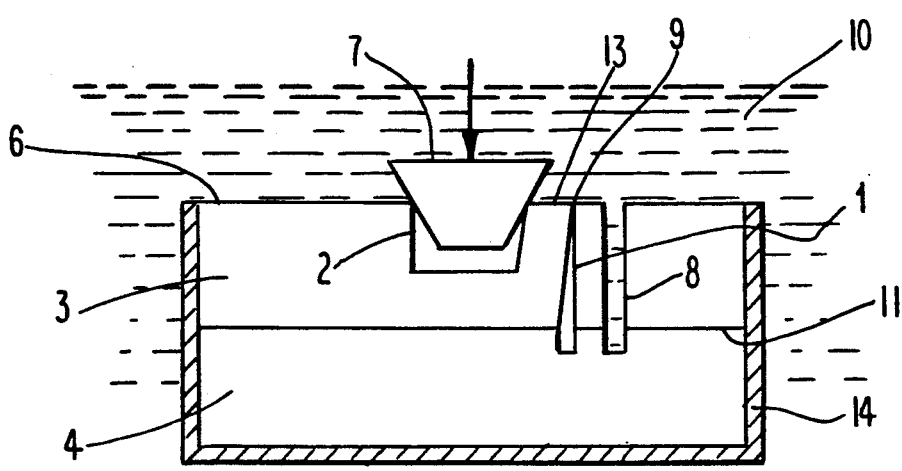
FIG. 3 is a cross sectional view of the inventive test specimen during a corrosion test taken through line 2—2 of FIG. 1.

The test specimen is shown during a testing procedure in FIG. 3. The crack gap 12 has been closed by the closing wall 13 to form a crack 9 on the cladding surface 6. This is accomplished by inserting wedge 7 into the shallow slot 2. A control slot 8 is also provided, cut to approximately the same width of the crack slot 1, in order to determine the effect of the test fluid 10 on the support base 3 and cladding layer 4. The control slot 8 is not partially closed to form a crack 9 as is the crack slot 1. By providing control slot 8, the test specimen can determine if the test fluid 10, the corrodant, actually penetrates the crack 9 by comparison study. The control slot 8 is preferably cut to the same depth as the crack slot 1. The control slot 8 may be cut to any depth necessary to model the specific system being studied.

The test is continued for a period of time until the effects of the corrodant, test fluid 10, can be determined. In the preferred embodiment modelling of a piping structure, the specimen is deposited into the annulus of an actual piping structure containing the test fluid 10. After the testing period is over, the specimen is retrieved and examined for corrosive wear and crack propagation. Preferably, the specimen is physically cut through the axis of the specimen perpendicular to the crack slot 1.

A specimen holder 14 is shown which encases the support base 4 and the sides of the cladding layer 3. The specimen holder 14 is preferably made of a material which will not corrode significantly in the test fluid 10. The specimen holder 14 is an optional element and is only absolutely necessary if the test fluid 10 violently corrodes the support base 4 such that the effects of the test fluid 10 upon the crack 9 are difficult to discern. The specimen holder 14 is preferred since the effects of the test fluid 10 on the crack 9 are isolated. In the preferred embodiment of testing a carbon steel support base 4 and a stainless steel cladding layer 3, the specimen holder 14 is a swagelock assembly.

The inventive specimen may be advantageously employed to test the corrosive effects of a corrodant upon a structure which has a support base 4 and a cracked cladding deposited thereto in which the cladding is the surface exposed to the corrodant. The test specimen ensures that the only path available for the corrodant to reach the support base 4 underlying the crack 9 is via a the crack 9 in the cladding 5 layer 3. The test specimen may also be provided with a control slot which does not inhibit the flow of the corrodant to the support base 4. In this way, it can be determined (1) if the corrodant will penetrate the crack; (2) the effects of the corrodant on the crack area; and (3) the effects of the corrodant on the structure if the corrodant is present in the internals of the multiple layer structure without allowing the corrodant to attack the support base 4 from any direction other than through the cladding layer 3.

We claim:

1. A process of testing the corrosiveness of chemicals on a cracked surface comprising:
    providing a test specimen which is comprised of a support base; a cladding layer deposited upon said support base and creating an interface between said support base and said cladding layer; a first slot cut into a portion of said cladding layer and not extending to the edge of said cladding layer, which creates a surface gap; and a second slot cut adjacent to said first slot and into a portion of said cladding layer and not extending to the edge of said cladding layer;
    inserting a wedge into said second slot for partially closing said surface gap and thereby creating a surface crack;
    supplying a corrodant to said test specimen for a test time period and
    determining corrosion of said test specimen.

2. The process of claim 1, including, prior to supplying the corrodant to said test specimen, encasing the support base in a specimen holder.

3. A process for testing the corrosiveness of chemicals on a cracked surface comprising providing a test specimen which is comprised of a support base, a cladding layer deposited upon said support base which creates an interface between said support base and said cladding layer;
    cutting a first slot into a portion of said cladding layer which creates a surface gap which does not extend to the edge of said cladding layer;
    cutting a second slot adjacent to said first slot and into a portion of said cladding layer, which does not extend to the edge of said cladding layer;
    inserting a wedge into said second slot and partially closing said surface gap creating a surface crack;
    supplying a corrodant to said test specimen for a test time period; and
    determining corrosion of said test specimen.

4. The process of claim 3, including, prior to supplying the corrodant to said test specimen, encasing the support base in a specimen holder.

* * * * *